United States Patent [19]

Steer

[11] Patent Number: 4,611,785

[45] Date of Patent: Sep. 16, 1986

[54] TUBE CLOSURE DEVICE

[75] Inventor: Peter L. Steer, Surrey, England

[73] Assignee: Craig Medical Products Limited, Reigate, England

[21] Appl. No.: 799,762

[22] Filed: Nov. 19, 1985

[30] Foreign Application Priority Data

Dec. 6, 1984 [GB] United Kingdom ............... 8430881

[51] Int. Cl.$^4$ ............................................ F16L 55/14
[52] U.S. Cl. ........................................ 251/4; 251/342; 251/349; 604/250; 604/256
[58] Field of Search ................... 251/4, 9, 342, 349, 251/350; 604/34, 250, 256, 262

[56] References Cited

U.S. PATENT DOCUMENTS

| | | | |
|---|---|---|---|
| 2,716,013 | 8/1955 | Tinker | 251/4 |
| 3,103,335 | 9/1963 | Martinez | 251/4 |
| 3,513,849 | 5/1970 | Vaillancourt et al. | 604/256 |
| 3,800,799 | 4/1974 | McWhorter | 604/256 |
| 4,055,179 | 10/1977 | Manschot et al. | 251/333 |
| 4,333,480 | 6/1982 | Villari | 128/767 |

FOREIGN PATENT DOCUMENTS

| | | | |
|---|---|---|---|
| 2551010 | 5/1977 | Fed. Rep. of Germany | 604/256 |
| 827874 | 2/1960 | United Kingdom . | |
| 890018 | 2/1962 | United Kingdom | 251/4 |
| 1128186 | 9/1968 | United Kingdom . | |
| 1323083 | 7/1973 | United Kingdom . | |
| 1343299 | 1/1974 | United Kingdom . | |
| 1447314 | 8/1976 | United Kingdom . | |
| 1445092 | 8/1976 | United Kingdom . | |
| 2058011 | 4/1981 | United Kingdom . | |
| 2101274 | 1/1983 | United Kingdom . | |
| 2061466 | 5/1984 | United Kingdom . | |

Primary Examiner—George L. Walton
Attorney, Agent, or Firm—Lawrence S. Levinson; Sanford J. Asman

[57] ABSTRACT

A tube closure device for closing a flexible tube has a first member having a tube portion for insertion into an end of the flexible tube, and a second member hinged to said first member and having means for securing the flexible tube to the second member. It also has a latch for releasably holding said first and second members in a hinged together "closed" position, and a plug for closing the tube portion of the first member when it is in its closed position.

6 Claims, 6 Drawing Figures

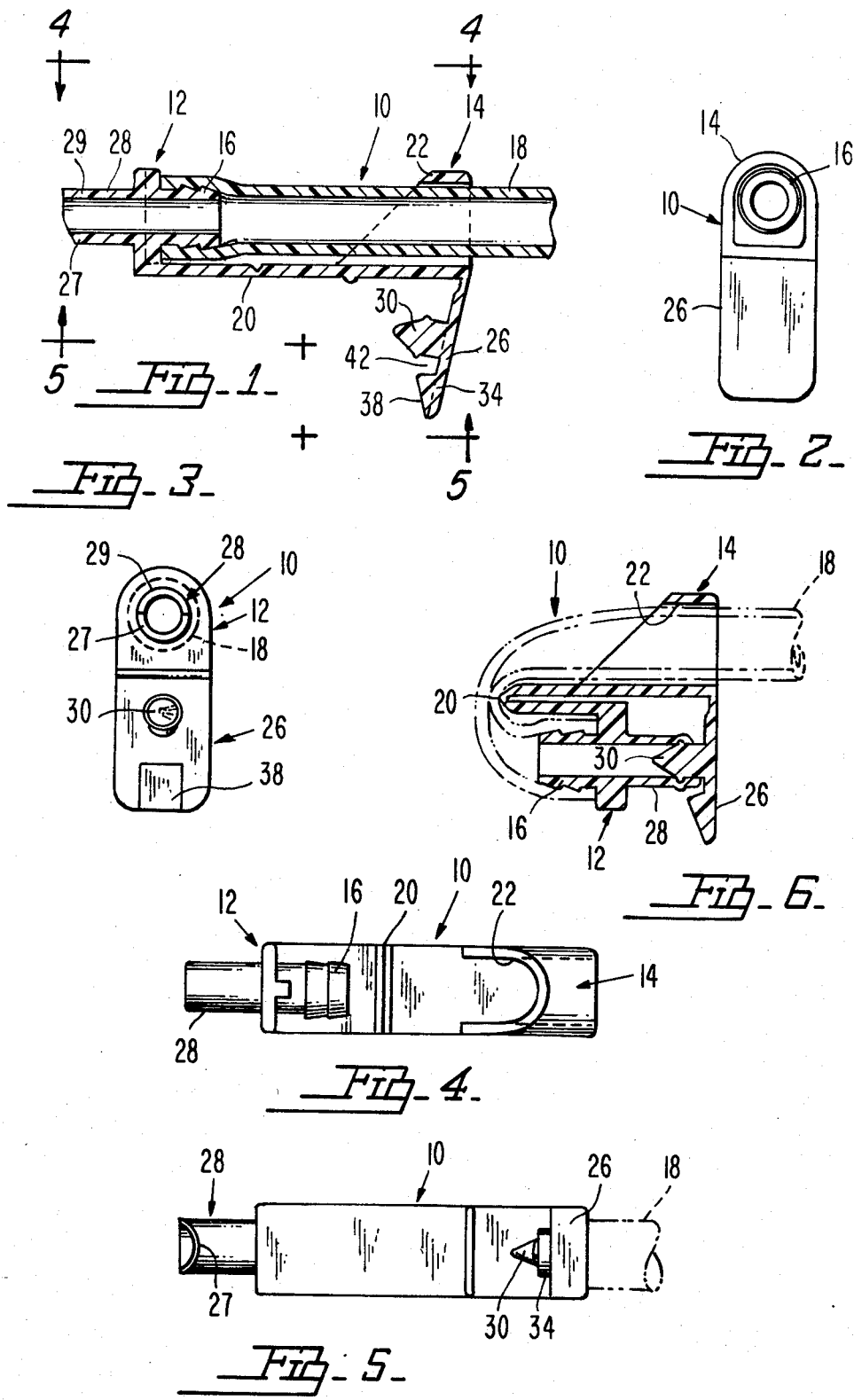

TUBE CLOSURE DEVICE

BACKGROUND OF THE INVENTION

The present invention relates to a tube closure device, particularly, but not exclusively, for closing a urine drainage tube.

In the past there have been problems with the leakage of valves, taps, or similar devices at the bottom of bags containing urine. One approach to the solution of these problems has been to make the valve or tap integral with the bag, as shown, for example, in British Patent No. 2101274, British Patent No. 2058011, British Patent No. 2061466, U.S. Pat. No. 4,333,480, and U.S. Pat. No. 4,055,179. Various clamping devices for pinching together the walls of flexible tubing or folding the tubing back on itself have also been proposed, as shown, for example, in British Patent No. 827874, British Patent No. 890018, British Patent No. 1128186, British Patent No. 1323083, British Patent No. 1343299, British Patent No. 1445092, and British Patent No. 1447314.

SUMMARY OF THE INVENTION

In the present invention is a tube closure device which is particularly free from leakage and which may be manufactured cheaply and easily. The invention provides a tube closure device for closing a flexible tube comprising a first member having a tube portion for insertion into an end of the flexible tube, a second member hinged to said first member and having means for securing the flexible tube to the second member, latch means for releasably holding said first and said second members in a hinged together "closed" position, and plug means for closing the tube portion of the first member in said closed position.

The device according to the invention is preferably constructed from a single piece of plastic. In the prefered embodiment, the device is molded in one piece from polypropylene.

BRIEF DESCRIPTION OF THE DRAWING

In the Drawing:

FIG. 1 shows a central axial cross-section through the preferred embodiment of the preferred embodiment of the tube closure device according to the present invention with the closure device in an open position;

FIG. 2 is a top plan view of the device of FIG. 1;

FIG. 3 is an bottom plan view of the device of FIG. 1;

FIG. 4 is a side view looking in the direction of the arrows 4—4 of FIG. 1;

FIG. 5 is a side view looking in the direction of the arrows 5—5 of FIG. 1; and

FIG. 6 diagrammatically illustrates the device in its "tube closed" position.

DETAILED DESCRIPTION OF THE PREFERRED EMBODIMENT

Referring to FIG. 1, the tube closure device 10 of the present invention is preferably molded in one piece from polypropylene. The device 10 comprises a first member 12 which has a tube portion 16 which may be fitted to the end of the flexible tube 18 which is to be closed. The first member 12 is held to a second member 14 by a thin portion 20 of the plastic which acts as a hinge. Polypropylene is a particularly suitable material for molding the device 10, since it can be repeatedly flexed without breaking.

The second member 14 includes a guide sleeve 22 for holding the flexible tube 18 in the second member 14.

The second member 14 also includes a latch and closure portion 26 which is capable of cooperating with a spigot 28 on the first member 12 when the device 10 is in its closed position, as illustrated in FIG. 6. The latch portion 26 includes a plug 30 which may be inserted into the end of the tube portion 16 when the device 10 is closed. The latch portion 26 also includes a catch 34 having a curved surface 38. The spigot 28 includes a side cutout so that part of its wall 27 does not extend out as far as another part of its wall 29. In the closing movement of the first member 12 relative to the second member 14, the portion 27 engages the surface 38, thereby moving the latch portion 26 in a counterclockwise direction, as shown in FIG. 1, permitting the free end of the tube 18 to be positioned such that the plug 30 is readily inserted in the tube 78. The end of the wall portion 29 is then located within the recess 42. The plug 30 closes the free end of the tube 18.

The device 10 can be easily opened and closed with one hand, and since it readily receives the free end of the tube 18, it does not require any special holster or support device forming part of, or attached to, the bag which is being drained.

As will be readily understood by those skilled in the art, the invention can be used to close any flexible tube when suitably dimensioned, but it is particularly suitable for closing urine drainage tubes.

The likelihood of leakage of a tube closed with the present invention is small, because the tube is closed both by folding the tubes back on itself across the hinge, and by the plugging the end of the tube portion of the first member. Furthermore, when the tube is vertically disposed, the formation of the fold in the tube by the device provides a U-bend, so that even if liquid does collect it will not be able to come out unless the whole device is inverted.

I claim:

1. A tube closure device for closing a flexible tube comprising:
    (a) a first member having a tube portion for insertion into an end of said flexible tube;
    (b) a second member hinged to said first member and having means for securing and supporting said flexible tube within a portin of said second member;
    (c) latch means integrally connected to said securing and supporting means for releasably holding said first and second members in a hinged together "closed" position; and
    (d) plug means integrally connected to said latch means for closing said tube portion of said first member in said closed position when said first member is folded to receive said plug means therein.

2. The device of claim 1 in which at least said first and second members are joined by an integral plastic hinge.

3. The device according to claim 2 in which there is a spigot on said first member which, in use, is placed in the end of a tube that is to be closed.

4. The device of claims 3 in which said second member includes a sleeve for receiving a tube to be closed.

5. The device according to claim 3 in which said spigot has a surface which engages the latch to open it during movement of said first member to its "closed" position, following which insertion of said plug holds the parts in said "closed" position.

6. The device of claim 5, wherein said device is made from polypropylene.

* * * * *